United States Patent

Blanc et al.

[11] 4,144,039
[45] Mar. 13, 1979

[54] SELECTIVE ABSORPTION PROCESS OF HYDROGEN SULPHIDE AND SULPHUR CONTAINING COMPOUNDS FROM A GASEOUS MIXTURE

[75] Inventors: Claude Blanc; Jean-Yves Chenard, both of Pau; Olivier Oliveau, Lescar, all of France

[73] Assignee: Societe Nationale Elf Aquitaine (Production), Paris, France

[21] Appl. No.: 867,291

[22] Filed: Jan. 5, 1978

[30] Foreign Application Priority Data

Jan. 6, 1977 [FR] France .................. 77 00274

[51] Int. Cl.² ............................................ B01D 19/00
[52] U.S. Cl. ...................................... 55/73; 423/226
[58] Field of Search ............... 55/73; 423/242, 563, 423/226

[56] References Cited

U.S. PATENT DOCUMENTS

| | | | |
|---|---|---|---|
| 2,083,213 | 6/1937 | Baehr et al. | 423/228 |
| 3,039,251 | 6/1962 | Kamlet | 55/473 |
| 4,020,149 | 4/1977 | Bosniaik | 55/73 |

Primary Examiner—Bernard Nozick
Attorney, Agent, or Firm—Brisebois & Kruger

[57] ABSTRACT

$H_2S$ is removed from gas containing $CO_2$ by a thioether, thioamide or alkyl thiocarbonate solvent.

9 Claims, 2 Drawing Figures

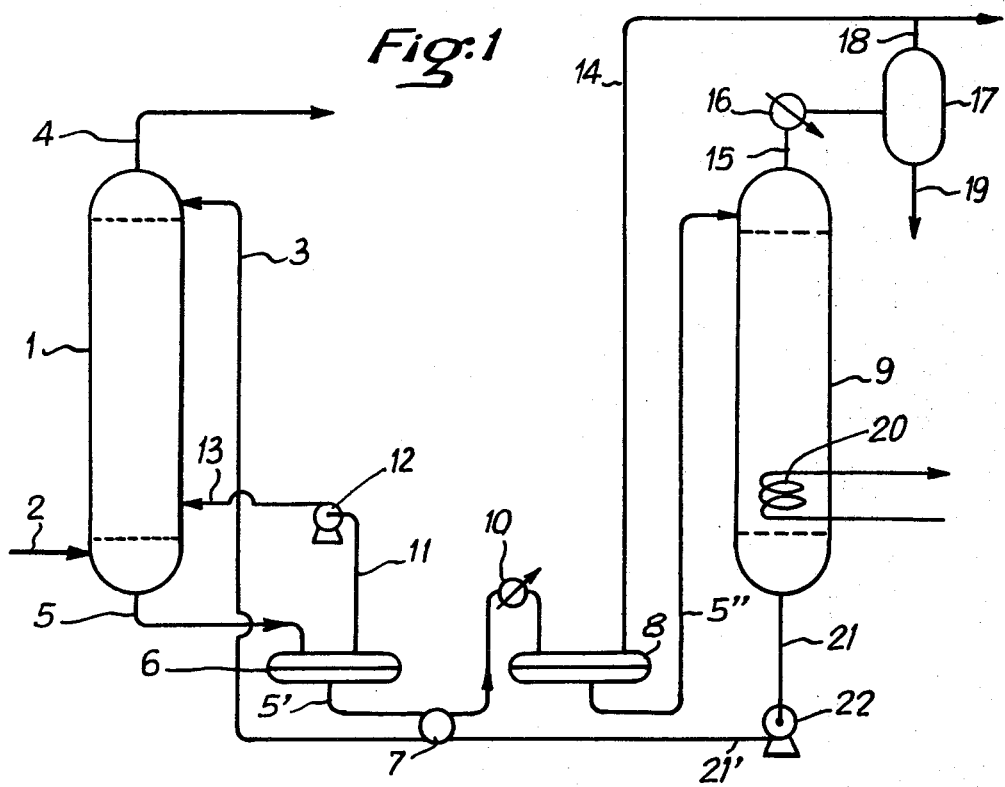
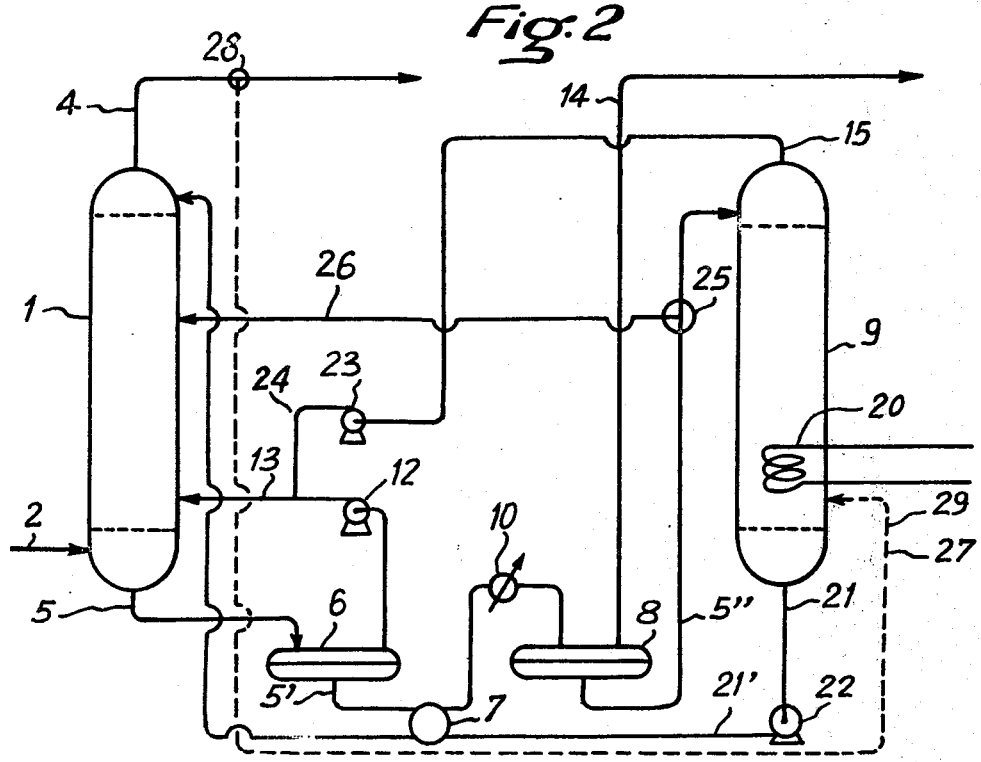

SELECTIVE ABSORPTION PROCESS OF HYDROGEN SULPHIDE AND SULPHUR CONTAINING COMPOUNDS FROM A GASEOUS MIXTURE

The present invention is concerned with the selective absorption of hydrogen sulphide and sulphur containing compounds from a gaseous mixture.

The gaseous mixtures to which the present process applies are natural or synthetic gases, hydrocarbon refining gases or wastes and more generally any gas or gaseous mixture containing $H_2S$ and $CO_2$. The $H_2S$ partial pressure in said gaseous mixtures must be at least 1 bar. All these gaseous mixtures contain hydrogen sulphide; they also contain $CO_2$ in quantities which are sometimes rather important and contain variable percentages of at least one of the group comprising hydrogen, $CO_2$, hydrocarbons, oxygen and steam.

The main treatment processes these gases are submitted to, especially the process based on the use of organic or aqueous solutions of primary or secondary amines, do not allow an effective absorption of $H_2S$ without totally absorbing $CO_2$; these processes are called "total deacidification processes".

In the treatment of a great number of industrial mixtures containing hydrogen sulphide and carbon dioxide, it appeared necessary, for technical and economic reasons, to make use of selective desulphuration process in order to absorb $H_2S$ and the other sulphur containing compounds while retaining the lowest proportion possible of $CO_2$.

Thus, for gaseous mixtures the $CO_2$ content of which is high when compared with the $H_2S$ content, total deacidification leads to $CO_2$-rich acidic gases which cannot be directly sent to the Claus reactors or to the thiochemical units, while selective desulphuration of the same mixtures leads to $H_2S$-rich gases (the volume percentage of which can be higher than 75%); this is the reason why it is thus possible to reduce the building costs and dimensions of the reactors while substantially improving the yields.

The treatment of such $H_2S$-rich acidic gases in Claus units has already been disclosed in French Pat. No. 2,277,765. Furthermore, in the case of natural gases containing a low content of $CO_2$ with respect to $H_2S$, it is economically advisable to maintain in the purified gas the $CO_2$ quantity specified by local commercial regulations; this is not possible in cases of total deacidification.

The preparation of gaseous mixtures to be used in the manufacture of carbon dioxide ice constitutes another example where any loss of $CO_2$ during the purification treatments results in proportional yield reduction. The interest of selective desulphuration has been recognized very soon. These already established methods, now in the public domain, which imply a selective desulphuration by liquid-gas washing under pressure, involved the use of chemical absorption agents, that is compounds chemically combinable with $H_2S$ and $CO_2$. These are essentially tertiary amines, the best known being triethanolamine, methyldiethanolamine, and the alkaline salts of dialkylaminoacetic and dialkylamino propionic acids. The selectivity of these known methods is based on an absorption kinetic which is different for $H_2S$ and $CO_2$; thus to minimize the losses in $CO_2$, the absorption conditions must be carefully controlled. These methods moreover present a certain number of drawbacks which are inherent to the conventional amine-based process, more particularly:

relatively low $H_2S$ capacity which only slowly increases with the partial pressure, thus necessitating the use of rather high solvent/feed ratios (expensive pumping costs), energy-expensive amine regeneration costs due to the significant exothermicity reaction and to the high value of specific mixing heat developed by the presence of high amounts of water.

The selective desulphuration process operated under pressure makes use of absorption agents called "physical absorption agents", i.e. which do not lead to chemical combinations with the constituents of the gases to eliminate. Generally in this case the solubility, in accordance with HENRY law, is proportional to their partial pressure in the gaseous phase. As these solvents are used in a pure state, their absorption capacities for $H_2S$ are much higher than those of aqueous amine solutions as soon as the $H_2S$ partial pressure goes beyond a few bars. The corresponding solvent/feed ratios are consequently much lower than those obtained when using amines. The regeneration of such physical solvents, the heat to weight ratios of which are much lower than those of the aqueous amine solutions, is less expensive and only needs a simple flash followed by moderate heating and/or a stripping with an $H_2S$-free gas (steam, purified gas, etc.).

These solvents moreover have the great advantage of physically absorbing a significant amount of the sulphur compounds present in the said gas. The $H_2S/CO_2$ selectivity is in such a case based on the solubility differences at conditions of equilibrium. Said selectivity is determined for each solvent by the solubility coefficients ratio $$\frac{K(H_2S)}{K(CO_2)}$$

at a given temperature. Most of the physical solvents, the use of which is suggested for total deacidification, have also been claimed for selective desulphurations; in point of fact, it has been found that most of the physical solvents dissolve, all factors being equal, more $H_2S$ than $CO_2$. For example, the journal *Erdoel Erdgas Zeitschrift* of October 1975, page 341, describes the use of the Selexol process, polyethylene glycol methyl ethers being used as solvents, for the selective desulphuration of a natural gas. The physical solvents used until now present however significant drawbacks when used as already disclosed, in particular:

generally mediocre selectivity which decreases as temperature increases, vapor pressure generally too high in the absorption conditions; this results in solvent losses which are not negligible in relation to the solvent costs, finally, and above all, an excessively high absorption capacity with respect to the aliphatic and aromatic hydrocarbons present in the gas.

The latter drawback is particularly important since, as is well known, the hydrocarbon content of the acidic acids to be treated in the Claus units must remain low, generally at about a few volume percent expressed as $CH_4$ equivalents, to avoid other numerous difficulties.

It is therefore necessary that the regeneration methods of usual physical solvents comprise a fractionated decompression comprising two or three successive flashes. The major part of the dissolved hydrocarbons is eliminated during the first flash and the recovered gas has to be recycled in the absorber, which involves a costly recompression.

The aim of the present invention is to determine a group of solvents which makes it possible to lessen considerably these drawbacks while maintaining the above-mentioned advantages to which the already known physical solvents lead. These are sulphur-containing solvents derived from previously known solvents principally by replacing in the initial molecules the whole or a part of the present oxygen atoms by sulphur atoms.

The present invention concerns a process for the selective absorption of the hydrogen sulphide contained in a gas mixture comprising, in addition to the hydrogen sulphide, carbon dioxide and at least one compound from the group comprising, for instance, hydrogen, carbon dioxide, hydrocarbons, nitrogen, oxygen and steam and which consists in washing the said gases with a pure solvent or with a solvent mixed with water in an absorption column maintained at a pressure higher than the atmospheric pressure and at a temperature between 5° and 80° C., is characterized in that the said solvent is chosen from the group consisting of thioethers, thioamides and alkyl thiocarbonates which are liquid at room temperature and present a viscosity at 40° C. lower than 10 centipoises and a vapor pressure lower than 0.25/n torr, (wherein n represents the number of sulphur atoms contained in the solvent molecule) and which lead to a weight ratio of absorbed $H_2S$ to absorbed $CO_2$ higher than 5 at a temperature of 40° C., the $H_2S$ (by weight) absorbed being at least equal at said temperature to one part (by weight) for 100 parts (by weight) of solvent per bar of $H_2S$ partial pressure, while the $CH_4$ absorbed is lower than 0.1 part (by weight) for 1000 parts (by weight) of solvent per bar of $CH_4$ partial pressure.

In some embodiments of the invention, the $H_2S$-selective solvent belongs to the thioethers having the formula:

$$R_4-X-R_2-(Y)_p-R_1-Z-R_3$$

wherein X, Y and Z represent either a sulphur atom or an oxygen atom, at least one sulphur atom being in the molecule, $R_3$ and $R_4$ represent a hydrogen atom or a $C_1$ to $C_3$ alkyl radical, $R_1$ and $R_2$ represent bivalent radicals having the formula $C_mH_{2m}$ where m = 1, 2 or 3 and p equals zero or 1.

Preferably, among these thioethers the following compounds can be used:
glycol thiodiethylene, or thiodiglycol having the formula

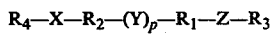
HO—$CH_2$—$CH_2$—S—$CH_2$—$CH_2$—OH this solvent has to be used in a solution with about 20% water in order for the viscosity to be lower than 10 centipoises.
dimethyldithiodiethylether having the formula

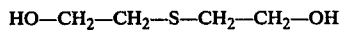
$CH_3$—S—$CH_2$—$CH_2$—O—$CH_2$—$CH_2$—S—$CH_3$

In other embodiments, the $H_2S$-selective solvent consists of a cyclic or linear thioamide having the following general formulae

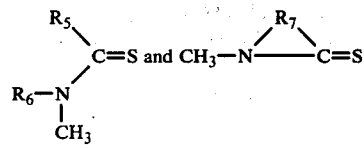

wherein $R_5$ and $R_6$ are $C_1$ to $C_3$ alkyl radicals and $R_7$ is a bivalent $C_2$ to $C_6$ aliphatic radical.

To this family belongs the N-methyl thiopyrrolidone having the formula

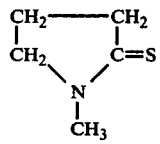

In other embodiments, the $H_2S$-selective solvent belongs to the cyclic or linear alkyl thiocarbonates having the formulae

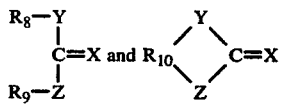

wherein X, Y and Z represent a sulphur or oxygen atom, with the molecule containing at least one sulphur atom, $R_8$ and $R_9$ are $C_1$ to $C_6$ alkyl radicals and $R_{10}$ is a bivalent $C_2$ to $C_6$ hydrocarbon radical.

To this family belong
ethyl monothiocarbonate having the formula

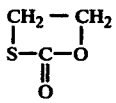

and ethylene dithiocarbonate having the formula

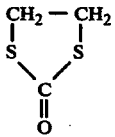

These families of solvents have been adopted as a result of a systematic study of about a hundred products which included, for the sake of comparison, all the already known solvents.

Table 1 compares the properties of three physical solvents, taken as a reference, with the same properties as the sulphur-containing solvents derived from the former by replacing an oxygen atom with a sulphur atom or of very closely related derivatives.

The change from the oxygen-containing solvent to the sulphur-containing solvent results in:
the lowering by only a small percentage of the $H_2S$ solubility; this reduction is not a very serious drawback as the solubility still remains very high and varies from 1.5 to 3% by weight per bar of $H_2S$ partial pressure at 40° C. It should be mentioned that this solubility increases considerably when the temperature decreases.

a considerable reduction of $CO_2$ solubility which is on the average 1.8 times reduction; thus the selectivity at 40° C., which is the $H_2S/CO_2$ solubilities ratio at said temperature, is for the sulphur containing solvents on the average twice the selectivity of the corresponding oxygen-containing solvents. The surprisingly high selectivities thus observed are further improved at low temperature (10° to 20° C.) since the $H_2S$ solubility increases far more rapidly than $CO_2$ solubility when temperature decreases.

a reduction of the saturated hydrocarbons solubility, all factors being equal, with respect to the oxygen-containing solvents taken as a reference. The solubility is 3 to 4 times lower and generally is lower than 0.01% by weight per bar of $CH_4$ partial pressure at 40° C.

TABLE 1

PROPERTIES OF THE SULPHUR-CONTAINING SOLVENTS COMPARED WITH THE CORRESPONDING OXYGEN-CONTAINING SOLVENTS (pressure: 10 bars, temperature: 40° C)

| SOLVENT | ABSORBED | | $H_2S/CO_2$ SELECTIVITY | $CH_4$ ABSORPTION (weight %) | VAPOUR PRESSURE (Torr) |
| --- | --- | --- | --- | --- | --- |
| | $H_2S$ (by weight) | $CO_2$ | | | |
| DIETHYLENEGLYCOL | 11.2 | 2 | 5.6 | 0.12 | 0.029 |
| THIODIETHYLENEGLYCOL | 10.6 | 1.2 | 8.8 | 0.17 | 0.0085 |
| N-METHYL-PYRROLIDONE | 35.7 | 5.5 | 6.5 | 1.58 | 0.88 |
| N-METHYLTHIO-PYRROLIDONE | 32 | 2.4 | 13.3 | 0.52 | 0.0115 |
| PROPYLENE CARBONATE | 16.3 | 4.5 | 3.63 | 0.45 | 0.05* |
| ETHYLENE MONOTHIOCARBONATE | 22 | 2.7 | 8.1 | 0.3 | 0.05* |

*at 26° C

Table 2 gives moreover some data concerning the absorption properties of one of the other solvents falling within the scope of the invention and consisting in dimethyl dithiodiethyl ether:

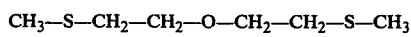

TABLE 2

| part % (by weight) - Pressure: 10 bars | |
| --- | --- |
| $H_2S$ absorption at 40° C: | 19 |
| $CO_2$ absorption at 40° C: | 4 |
| $H_2S/CO_2$ selectivity at 40° C: | 4.75 |
| $H_2S$ absorption at 15° C: | 57 |
| $CO_2$ absorption at 15° C: | 6 |
| $H_2S/CO_2$ selectivity at 15° C: | 9.5 |
| $CH_2$ absorption at 40° C: | 0.09 |
| $CH_4$ absorption at 0° C: | 0.1 |

Due to these low solubilities, the recycling of the gas recovered during the first flash can be considerably reduced; this leads to a substantial reduction in the operating costs as compared with the process described in the prior art.

Furthermore, the substitution of one or several oxygen atoms by one or several sulphur atoms in a molecule leads to a significant reduction of the vapor pressure of the corresponding solvent, which is particularly advantageous for the sulphur-containing solvents according to the present invention since any solvent loss in the purified gas results not only in additional costs but also in an increased total sulphur content of the purified gas, which is precisely what one tries to avoid.

Further characteristics and advantages of the invention will be better understood from the following description in reference to the attached flow sheets giving as an illustration preferred forms of plants according to the present invention.

FIG. 1 is a flow sheet of an industrial plant comprising an absorption column fed at only one level in solution.

FIG. 2 is a flow sheet of an industrial plant comprising an absorption column fed at several levels in solution.

The flow sheet of FIG. 1 relates to the selective absorption of the $H_2S$ contained in a gaseous mixture, said flow sheet comprising an absorption column 1 in the bottom of which an untreated gas is fed by inlet pipe 2 while in its upper part the solvent is fed through inlet pipe 3; the top of said column further comprises an outlet conduit 4 for discharging the purified gas while its bottom is provided with an outlet conduit 5 for the $H_2S$-enriched solvent.

Outlet conduit 5 enters the upper part of a high pressure degassing drum 6 at the bottom of which an outlet conduit 5' discharges the solution which, after passage through a heat exchanger 7, is fed in the upper part of a low pressure degassing drum 8 at the bottom of which the solution is discharged through outlet conduit 5".

A heating device 10 usually fed with steam is provided on said outlet conduit 5' between heat exchanger 7 and low pressure degassing drum 8.

A conduit 11, issuing from the high pressure degassing drum 6, allows the collection of hydrocarbon gases consisting essentially of methane; said gases after passage through compressor 12 are fed by pipe 13 into the lower part of absorption column 1. From low pressure degassing drum 8 issues a discharge pipe 14 which evacuates a solvent-free gaseous mixture.

A conduit 15 issuing from the top of regeneration column 9, after passage through cooling system 16, enters the middle part of decanter 17.

A conduit 18 issuing from the top of said decanter 17 leads the gaseous wastes to discharge pipe 14, while a conduit 19 at the bottom of decanter 17 allows the discharge of water.

The heating of the lower part of regneration column 9 is either operated directly by the introduction of overheated steam in the column or indirectly by means of a conventional reboiler 20.

At the lowest part of regeneration column 9, a conduit 21 collects the regenerated solvent which, by means of recirculation pump 22, is recycled through pipe 21' to the upper part of absorption column 1, after passage through heat exchanger 7.

The operating conditions of such an installation are the following:

the untreated gas, at a pressure of between 10 and 80 bars, is fed by inlet pipe 2 at the bottom of column 1.

in absorption column 1 a countercurrent washing (or stripping) is carried out; the liquid solvent is injected at the upper part of column 1 and discharged at the lower part after enrichment mainly in $H_2S$ and, in a lower proportion, in $CO_2$.

The thus enriched solvent is then fed successively into a high pressure degassing drum 6 where its pressure is lowered to an intermediary value which is a function of the initial pressure of the untreated gas, into a low pressure degassing drum 8, where its pressure is further lowered to about 2 bars and then into the regeneration column 9 at said pressure of about 2 bars, where the acidic gases are further eliminated due to the temperature increases produced by steam at the lower part of regeneration column 9.

In high pressure degassing drum 6, the hydrocarbons are removed from the solution and, after recompression by means of a compressor are injected in the lower part of absorption column 1.

In low pressure degassing drum 8, most of the $H_2S$ and $CO_2$ are removed from the solution and form a gaseous flow which via conduit 14 is sent to a sulphur-producing plant or a thiochemistry plant.

The regnerated solvent is recycled by circulation pump 22 to the upper part of absorption column 1.

FIG. 2 is a flow sheet showing the selective absorption of $H_2S$ contained in a gaseous mixture, the solvent being fed at several levels and at various concentrations in the absorption column, the regeneration occurring by means of gas freed of any sulphur compounds. The plant shown in FIG. 2 is a more complex one than that represented in FIG. 1 which may be modified according to different embodiments.

The flow sheet on FIG. 2 comprises the same main items as shown in FIG. 1, that is absorption column 1, regeneration column 9, high pressure and low pressure degassing drums, 6 and 8 respectively, outlet conduits 5, 5' and 5" for the $H_2S$-enriched solvent, conduit 21 and pipe 21' for the regenerated solvents, heat exchanger 7 in which conduit 5' and pipe 21' pass, heating device 10, circulation pump 22 and compressor 12.

Conduit 11 issuing from the high pressure degassing drum 6 leads to compressor 12, the outlet of which is connected to absorption column 1 through conduit 13, and associated by an injector means placed at the lower portion of absorption column 1.

Conduit 15 issuing from the top of regeneration column 9, after passing through compressor 23, continues as conduit 24 which leads to conduit 13.

Outlet conduit 5", which joins the bottom of low pressure degassing drum 8 to the upper part of regeneration column 9, comprises a valve system 25 which allows part of the liquid flow of outlet conduit 5" to be sent to absorption column 1 via pipe 26 and associated injector means is usually placed at a level between the middle and ⅔ of the absorption column height.

Conduit 27 connects pipe 4 to the lower part of regeneration column 9, via controlled gas offtake 26 and injection means 29.

FIG. 2 shows by way of example how to introduce at different levels of column 1 and at different concentrations the solvent fed by conduits 13 and 26. It also shows how to inject at the bottom of regeneration column 9 via conduit 27 a part of the gas offtake issuing from the top of column 1 through pipe 4.

The invention will now be described in the following non-limiting example of operating conditions and compositions of the various gaseous and liquid fractions obtained in the plant such as shown on FIG. 1 flow sheet.

EXAMPLE 1

An untreated natural gas having the following composition (by volume)
$CH_4$: 75%
$H_2S$: 15%
$CO_2$: 9.8%
$C^{2+}$: 0.2% is fed to a preliminary separator of a selective desulphuration plant at a temperature of 20° C. and a total pressure of 80 bars. The untreated gas inflow rate is 500,000 $Nm^3/d$; said gas is stripped by countercurrent circulation in absorber of 12.5 t/h of N-methylthiopyrrolidone. The temperature at the bottom of the absorber is 40° C. The enriched solvent is then flashed in a degassing drum at a pressure of 25 bars. The resulting gaseous phase consists in 0.2 t/h of a gas comprising (by volume):
$CH_4$: 31.4%
$H_2S$: 46%
$CO_2$: 22.6%

Thus, this corresponds to a volume flow rate of 0.77% of the inflow rate. The solvent is regenerated by heating at 120° C., flashing and stripping with steam.

The acidic gas obtained, to be used for feeding a Claus unit, has the following composition (by volume) expressed as dry gas:
$H_2S$: 97.1%
$CH_4$: 0.2%
$CO_2$: 2.7%

The purified gas meets the regulations which require a maximum proportion of ¼ $H_2S$ grain for 100 SCF (the standard condition being 15° C. and 750 Hg mm).

EXAMPLE 2

The same gas as used in Example 1 is submitted to a selective desulphuration. The inflow rate is 2,000,000 $Nm^3$/day. Said gas is stripped by countercurrent circulation of 82.6 t/h of dimethyldithiodiethylether in an absorber the bottom temperature of which is 40° C. The enriched solvent discharged is flashed, as described in Example 1 above, at a pressure of 33.3 bars. The gas thus obtained has the following composition:
$CH_4$: 44% by volume
$H_2S$: 35%
$CO_2$: 21%

The weight flow rate of the fuel gas is 1.24 t/h, that is 1.55% of the untreated gas inflow rate. The acidic gas obtained after regeneration of the solvent has the following composition:
$H_2S$: 91%
$CO_2$: 7.8%
$CH_4$: 1.2%

The purified gas thus conforms with standard regulations.

What is claimed is:

1. A process for the selective desulphuration of a gaseous mixture comprising, in addition to hydrogen sulphide, carbon dioxide and at least one compound from the groups comprising hydrogen, carbon dioxide, hydrocarbons, nitrogen, oxygen and steam and which comprises washing the said gases with a pure solvent or with a solvent mixed with water in an absorption column maintained at a pressure higher than the atmospheric pressure and at a temperature between 5° and 80° C., said solvent is selected from the group consisting of thioethers, thioamides and alkyl thiocarbonates which are liquid at room temperature and present a viscosity at 40° C. lower than 10 centipoises and a vapor pressure lower than 0.25/n torr, wherein n represents the number of sulphur atoms in the solvent molecule, and which lead to a weight ratio of absorbed $H_2S$ to absorbed $CO_2$ higher than 5 at a temperature of 40° C., the $H_2S$ by weight absorbed being at least equal at said temperature to one part by weight for 100 parts by weight of solvent per bar of $H_2S$ partial pressure, while the $CH_4$ absorbed is lower than 1.0 part by weight for 1000 parts by weight of solvent per bar of $CH_4$ partial pressure.

2. A process according to claim 1 in which the $H_2S$-selective solvent is a thioether having the formula:

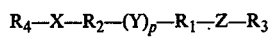

wherein X, Y and Z are either sulphur or oxygen, at least one sulphur atom being in the molecule, $R_3$ and $R_4$ are hydrogen or alkyl, $R_1$ and $R_2$ represent bivalent radicals having the formula $C_mH_{2m}$ where m = 1, 2 or 3 and p equals zero or 1.

3. A process according to claim 2, in which the $H_2S$-selective solvent is glycol thiodiethylene, or thiodiglycol having the formula:

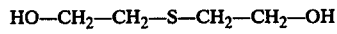

this solvent being used in a solution with about 20% water.

4. A process according to claim 2, in which the $H_2S$-selective solvent is dimethyldithiodiethylether having the formula:

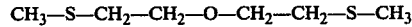

5. A process according to claim 1, in which the $H_2S$-selective solvent consists of a cyclic or linear thioamide having the general formulae:

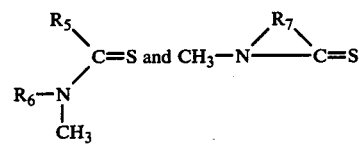

wherein $R_5$ and $R_6$ are $C_1$ to $C_3$ alkyl radicals and $R_7$ is a bivalent $C_2$ to $C_6$ aliphatic radical.

6. A process according to claim 5, in which the $H_2S$-selective solvent is N-methyl thiopyrrolidone having the formula:

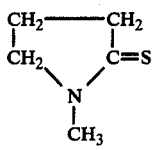

7. A process according to claim 1, in which the $H_2S$-selective solvent belongs to the cyclic or linear alkyl thiocabonates having the formulae:

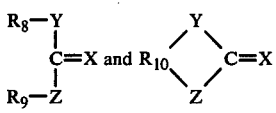

wherein X, Y and Z represent a sulphur or oxygen atom, the molecule containing at least one sulphur atom, $R_8$ and $R_9$ are $C_1$ to $C_6$ radicals and $R_{10}$ is a bivalent $C_2$ to $C_6$ hydrocarbon radical.

8. A process according to claim 7, in which the $H_2S$-selective solvent is ethyl monothiocarbonate having the formula:

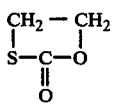

9. A process according to claim 7, in which the $H_2S$-selective solvent is ethyldithiocarbonate having the formula:

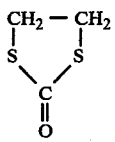

* * * * *